United States Patent [19]

Logan

[11] 4,026,667
[45] May 31, 1977

[54] SULFIDE DETECTION DEVICE

[75] Inventor: Douglas Patton Logan, Coraopolis, Pa.

[73] Assignee: Calgon Corporation, Pittsburgh, Pa.

[22] Filed: Aug. 11, 1976

[21] Appl. No.: 713,543

[52] U.S. Cl. .......................... 23/230 R; 23/253 TP; 252/408
[51] Int. Cl.² ........................................ G01N 31/22
[58] Field of Search .................. 23/230 R, 253 TP; 252/408

[56] References Cited

UNITED STATES PATENTS

| | | | |
|---|---|---|---|
| 3,412,038 | 11/1968 | Plantz | 23/230 R X |
| 3,433,597 | 3/1969 | Lyshkow | 23/230 R X |
| 3,672,842 | 6/1972 | Florin | 23/230 R |
| 3,920,402 | 11/1975 | Afanasiev et al. | 23/255 E X |

*Primary Examiner*—Robert M. Reese
*Attorney, Agent, or Firm*—Rudolph J. Anderson, Jr.; Harry E. Westlake, Jr.; Martin L. Katz

[57] ABSTRACT

Solid metal carboxylate composition which is used to detect the presence of sulfide in high pH aqueous streams.

8 Claims, No Drawings

SULFIDE DETECTION DEVICE

This invention relates to a device to detect the presence of sulfide ions in high pH aqueous streams.

More particularly, this invention relates to a solid metal carboxylate composition which turns black upon contact of sulfide or hydrosulfide ions in aqueous systems.

Often, when drilling for producing hydrocarbons, hydrogen sulfide is encountered. This gas presents two hazards to operating personnel. It is a flammable, explosive, toxic gas and it can result in catastrophic failure of high strength drill pipe drilling equipment. In neutral or low pH aqueous-based systems, hydrogen sulfide is readily detected by its rotten egg odor. However, in alkaline systems, hydrogen sulfide is neutralized to hydrosulfide and sulfide ions, which are odorless and can be difficult to detect.

In many aqueous-based mud systems used in drilling operations, the pH of the mud is maintained at 9 or higher. At this pH, less than 0.6% of the total sulfide exists as hydrogen sulfide. Therefore, the mud can hold an appreciable quantity of sulfide before its presence is detected as $H_2S$ by smell or chemical analysis. But at the point of gas intrusion into the system, the hydrogen sulfide entering the borehole results in a neutral to acidic condition. This condition can lead to rapid, severe localized corrosion of the high strength drill pipe. When sulfide or hydrosulfide are detected in a drilling system, appropriate safety precautions can be initiated and a suitable corrosion control program started.

Prior art techniques for the detection of the presence of sulfide or hydrosulfide ions required the acidification of a sample of the aqueous stream being tested in the presence of lead acetate paper, or the acidification and oxidation-reduction titration with iodate via the iodine demand technique. These techniques required the presence of a chemical technician and/or sophisticated apparatus to determine the presence of sulfide as compared to the present invention within.

Accordingly, it is an object of this invention to provide a device which detects the presence of sulfide or hydrosulfide ions in high pH aqueous streams.

It is a further object of this invention to provide a device which may be used directly on the aqueous system being evaluated.

It is still a further object of this invention to provide a device which is economical and does not require highly-trained personnel to operate.

These and other objects of this invention are accomplished by the composition of the present invention which comprises:

a. 20 to 60 weight percent, preferably 40 to 50 weight percent, of a carboxylic acid, preferably a water-insoluble fatty carboxylic acid, as for example those acids with five to 22 carbon atoms such as caproic acid, valeric acid, palmitic acid, lauric acid, stearic acid or soya acid;

b. 10 to 50 weight percent, preferably 30 to 40 weight percent, of a metal salt, preferably a water-soluble salt, as for example the acetate salts of lead, cobalt, nickel, copper or iron;

c. 5 to 35 weight percent, preferably 9 to 29 weight percent, of a solid wax, as for example paraffin wax, candle wax or microcrystalline wax;

d. 0 to 10 weight percent, preferably 0 to 1 weight percent, of a nonionic surfactant, preferably an ethoxylated alcohol that is soluble in aromatic solvents and water, as for example Plurafac A-38, Igepal CO-850 and Emulphor EL-719. (Plurafac is the trade name for ethoxylated alcohols made by BASF Wyandotte Corporation, Wyandotte, Mich. Emulphor, an ethoxylated vegetable oil, and Igepal, an ethoxylated alkyl phenol surfactant, are manufactured by GAF Corporation, New York, N.Y.)

e. 0 to 2 weight percent, preferably 0 to 0.05 weight percent, of an oil-soluble dye, as for example red such as Sudan Red O or Sudan Red GGA (GAF Corporation, New York, N.Y.) or blue such as Calco Oil Blue (American Cyanamid Company, Wayne, N.J.).

The composition of the present invention may be used to detect the presence of sulfide or hydrosulfide ions in alkaline aqueous fluid streams or systems. This composition may be molded or formed into any desired geometric shape, as for example tubular sticks, rectangular sticks or discs. It also may be used to coat an inert carrier, as for example a plastic indicator stick.

In use, the composition is placed in contact with the fluid stream in any manner, as for example by partial insertion into the fluid stream, and upon contact with the sulfide or hydrosulfide ion in the fluid stream, the lightly colored stick will undergo a color change to black as the following chemical reaction takes place:

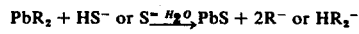

$R = $ carboxylate

If it is desired to reuse the sulfide detector of the instant invention, it is merely necessary to scrape off the portion of the detector which has undergone the chemical reaction and color change, thereby exposing a new and clean surface.

The composition of the present invention may be illustrated by the following examples.

EXAMPLE 1

50 grams of stearic acid, having a melting point of 70° C, is heated to 100° C and 37.5 grams of lead acetate trihydrate is added slowly with stirring to the hot stearic acid. The solution is heated to 118°–120° C to remove the acetic acid. 11.5 grams of candle wax, 1.0 gram of Plurafac A-38 and 0.01 gram of dye (Sudan Red O) are added to the hot lead stearate with stirring. The hot mixture is then placed in a tubular form containing a wick and allowed to cool and solidify, thereby forming a tubular stick.

EXAMPLE 2

20 grams of valeric acid is added to 25 grams of nickel acetate tetrahydrate and the mixture heated to remove the water and acetic acid. Then 20 grams of microcrystalline wax and 2.5 grams of Igepal CO-850 are added. The hot solution is added to molds and allowed to cool and solidify.

EXAMPLE 3

40 grams of lauric acid is heated to 100° C and 20 grams of copper acetate hydrate added with stirring. Following removal of the acetic and water by distillation, 35 grams of paraffin wax and 0.75 gram of Plurafac A-38 are added and the solution stirred. The melt is added to tubular molds and allowed to solidify.

EXAMPLE 4

50 grams of palmitic acid and 25 grams of cobalt acetate tetrahydrate are heated to 120° C to remove water and acetic acid. 7.5 grams of candle wax and 4.0 grams Emulphor EL-719 are added and allowed to dissolve. The solution is poured into molds and allowed to solidify.

I claim:
1. A sulfide or hydrosulfide detection composition consisting essentially of:
   a. 20 to 60 weight percent of a carboxylic acid;
   b. 10 to 50 weight percent of a metal salt;
   c. 5 to 35 weight percent of a solid wax;
   d. 0 to 10 weight percent of a nonionic surfactant; and
   e. 0 to 2 weight percent of an oil-soluble dye.
2. A composition as in claim 1 wherein the metal salt is water-soluble.
3. A composition as in claim 1 wherein the metal salt is an acetate salt.
4. A composition as in claim 1 which consists essentially of:
   a. 40 to 50 weight percent of a carboxylic acid having from 5 to 22 carbon atoms;
   b. 30 to 40 weight percent of a water-soluble metal acetate salt;
   c. 9 to 29 weight percent of a solid wax;
   d. 0 to 1 percent of an ethoxylated nonionic surfactant; and
   e. 0 to 0.5 weight percent of an oil-soluble dye.
5. A composition as in claim 1 wherein the carboxylic acid has from 5 to 22 carbon atoms.
6. A composition as in claim 5 wherein the carboxylic acid is selected from the group consisting of caproic acid, lauric acid, stearic acid, soya acid, valeric acid and palmitic acid.
7. A method of detecting the presence of sulfide or hydrosulfide which comprises contacting a fluid stream with a composition consisting essentially of:
   a. 20 to 60 weight percent of a carboxylic acid;
   b. 10 to 50 weight percent of a metal salt;
   c. 5 to 35 weight percent of a solid wax;
   d. 0 to 10 weight percent of a nonionic surfactant; and
   e. 0 to 2 weight percent of an oil-soluble dye.
8. A method as in claim 7 wherein the composition consists essentially of:
   a. 40 to 50 weight percent of a carboxylic acid having from 5 to 22 carbon atoms;
   b. 30 to 40 weight percent of a water-soluble metal acetate salt;
   c. 9 to 29 weight percent of a solid wax;
   d. 0 to 1 percent of an ethoxylated nonionic surfactant; and
   e. 0 to 0.5 weight percent of an oil-soluble dye.

* * * * *

UNITED STATES PATENT OFFICE
CERTIFICATE OF CORRECTION

PATENT NO. : 4,026,667
DATED : May 31, 1977
INVENTOR(S) : Douglas Patton Logan

It is certified that error appears in the above-identified patent and that said Letters Patent are hereby corrected as shown below:

Column 2, line 9, "0.05" should read -- 0.5 --.

Column 2, line 65, after "acetic" add -- acid --.

Signed and Sealed this twenty-third Day of August 1977

[SEAL]

Attest:

RUTH C. MASON
Attesting Officer

C. MARSHALL DANN
Commissioner of Patents and Trademark